United States Patent
Lai et al.

(10) Patent No.: US 6,893,624 B2
(45) Date of Patent: May 17, 2005

(54) HIGH ACTIVITY SMALL CRYSTAL ZSM-12

(75) Inventors: Wenyih F. Lai, Bridgewater, NJ (US); Ivy D. Johnson, Laurenceville, NJ (US)

(73) Assignee: ExxonMobil Chemical Patents Inc., Houston, TX (US)

(*) Notice: Subject to any disclaimer, the term of this patent is extended or adjusted under 35 U.S.C. 154(b) by 94 days.

(21) Appl. No.: 10/294,780

(22) Filed: Nov. 15, 2002

(65) Prior Publication Data

US 2004/0097363 A1 May 20, 2004

(51) Int. Cl.⁷ ............................................. C01B 39/42

(52) U.S. Cl. ............... 423/705; 423/716; 423/DIG. 33; 585/475

(58) Field of Search ............................. 423/705, 716, 423/DIG. 33; 585/475

(56) References Cited

U.S. PATENT DOCUMENTS

| | | |
|---|---|---|
| 3,832,449 A | 8/1974 | Rosinski et al. |
| 4,391,785 A | 7/1983 | Rosinski et al. |
| 4,452,769 A | 6/1984 | Chu et al. |
| 4,537,758 A | 8/1985 | Chu et al. |
| 4,539,193 A | 9/1985 | Valyocsik |
| 4,552,738 A | 11/1985 | Rubin |
| 4,552,739 A | 11/1985 | Kühl |
| 4,585,637 A | 4/1986 | Rubin |
| 4,585,746 A | 4/1986 | Valyocsik .................. 502/62 |
| 4,665,268 A * | 5/1987 | Lee et al. .................. 585/640 |
| 5,021,141 A | 6/1991 | Rubin |
| 5,192,521 A | 3/1993 | Moini et al. ............... 423/713 |
| 5,350,722 A * | 9/1994 | Joly et al. .................. 502/64 |
| 5,905,051 A | 5/1999 | Wu et al. .................... 502/60 |
| 5,942,651 A | 8/1999 | Beech, Jr. et al. .......... 585/475 |
| 2002/0150533 A1 * | 10/2002 | Malek |

FOREIGN PATENT DOCUMENTS

| | | | |
|---|---|---|---|
| EP | 167 232 | 8/1986 | ........... C01B/33/28 |
| JP | 11100381 A | * 4/1999 | |

OTHER PUBLICATIONS

Cejka, J. et al., "(Al)–ZSM–12: Synthesis and modification of acid sites", Studies in Surface Science and Catalysis 142, R. Aiello, G. Giordano and F. Testa (Editors), copyright 2002 Elsevier Science B.V.

Ernst, S. et al., "Synthesis of zeolite ZSM–12 in the system (MTEA)2O–Na2O–SiO2–Al2O3–H2O", Zeolites, vol. 7, September, pp. 458–462; 1987.

Katovic, A. et al., "An NMR Characterization of MTW Zeolite Synthesized in Presence of TEA+ and/or MTEA+ Cations", H.K.Beyer, H.G. Karge, I. Kiriesi and J.B.Nagy (Eds)., Studies in Surface Science and Catalysis, vol. 94, pp. 333–340, Elsevier Science B.V., 1995.

Xiang, Shouhe et al., "Studies on the Synthesis of ZSM–12 Zeolite of Low SiO2/Al2O3 Ratio", abstract, Database Compendex Online, XP002271458, & Shiyou Xuebao Shiyou Huagong, Mar. 1987.

Zhao, Xiusong et al., "Synthesis of Zeolite ZSM–12", Database CA Online, XP002271476 & Yingyong Huaxue (1993), 10(6), 80–2.

* cited by examiner

*Primary Examiner*—David Sample

(57) ABSTRACT

A porous, crystalline material is described having the framework structure of ZSM-12 and a composition involving the molar relationship:

$$X_2O_3 : (n)YO_2$$

wherein X is a trivalent element, Y is a tetravalent element and n is less than 60. The material has an average crystal size of the material is less than 0.1 micron and a Diffusion Parameter for mesitylene of at least $1000 \times 10^{-6}$ sec$^{-1}$ when measured at a temperature of 100° C. and a mesitylene pressure of 2 torr.

19 Claims, 5 Drawing Sheets

HIGH ACTIVITY SMALL CRYSTAL ZSM-12

FIELD

This invention relates to a high activity, small crystal ZSM-12, its synthesis and its use in catalytic processes, particularly in the conversion of $C_9+$ aromatic hydrocarbons to xylenes.

BACKGROUND

ZSM-12 and its conventional preparation in the presence of a tetramethylammonium or tetraethylammonium directing agent are taught by U.S. Pat. No. 3,832,449, the entire disclosure of which is incorporated herein by reference. ZSM-12 has a distinctive X-ray diffraction pattern which distingishes it from other known crystalline materials.

U.S. Pat. No. 4,391,785 discloses a method for the synthesis of ZSM-12 from a reaction mixture comprising, as a directing agent, a compound selected from the group consisting of a dimethyl pyridinium halide and a dimethyl pyrrolidinium halide.

U.S. Pat. Nos. 4,452,769 and 4,537,758 disclose methods for synthesizing ZSM-12 from a reaction mixture containing methyltriethylammonium ions as the directing agent. However, these patents are primarily directed to producing high $SiO_2/Al_2O_3$ ratio forms of ZSM-12, greater than 80 in the case of the '769 patent and greater than 200 in the case of the '758 patent. Moreover, one of the stated advantages in the '769 patent of using methyltriethylammonium ions as the directing agent is the production of large crystal size materials.

Other organic directing agents that have been used to synthesize ZSM-12 include bis(dimethylpiperidinium) trimethylene ions (see U.S. Pat. No. 4,539,193), benzyltriethylammonium ions (see U.S. Pat. No. 4,552,738), dibenzyldiethylammonium ions (see EP-A-167,232), dimethyldiethylammonium ions (see U.S. Pat. No. 4,552,739), benzyltrimethylammonium ions (see U.S. Pat. No. 4,585,637), bis(N-methylpyridyl)ethylinium ions (see U.S. Pat. No. 4,5852,746), hexamethyleneimine (U.S. Pat. No. 5,021,141) and bis(methylpyrrolidinium)-diquat-n, where n=4, 5 or 6 (see U.S. Pat. No. 5,192,521).

Although influenced by variables such as the silica/alumina molar ratio of the reaction mixture, temperature and stirring, the crystal morphology of synthetic zeolites, such as ZSM-12, is mainly dominated by the choice of directing agent used in the crystallization. For example, in the case of ZSM-12, needle-shaped crystals can be produced using a benzyltrimethylammonium directing agent, rice-shaped crystals can be made in the presence of tetraethylammonium salts, and bundles of hexagonal platelets can be prepared from with a hexamethyleneimine directing agent.

The control of zeolite crystal morphology is very important from the standpoint of activity and stability enhancement. For catalytic applications, small crystal size is always the desired preference for high activity and stability because of the higher surface area, and hence the shorter diffusion path, of small crystal materials. In addition since zeolite activity is associated with the aluminum atoms in the zeolite framework, the lower the $SiO_2/Al_2O_3$ ratio of the zeolite, the higher its acidity. To date, most synthesis routes for ZSM-12 have led to the production of either small crystal materials or materials with a low $SiO_2/Al_2O_3$ ratio. In general, however, it has been difficult to synthesize high purity ZSM-12 which has both the attributes of small crystal size and low $SiO_2/Al_2O_3$ ratio.

An object of the present invention is to provide a small crystal, high activity form of ZSM-12 which exhibits enhanced activity in the conversion of $C_9+$ aromatic hydrocarbons to xylenes.

It is to be appreciated that, although ZSM-12 is normally synthesized as an aluminosilicate, the framework aluminum can be partially or completely replaced by other trivalent elements, such as boron, iron and/or gallium, and the framework silicon can be partially or completely replaced by other tetravalent elements such as germanium.

SUMMARY

In one aspect, the invention resides in a porous, crystalline material having the framework structure of ZSM-12 and a composition involving the molar relationship:

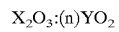

$$X_2O_3:(n)YO_2$$

wherein X is a trivalent element, Y is a tetravalent element and n is less than 60, wherein the average crystal size of the material is less than 0.1 micron and wherein the material has a Diffusion Parameter for mesitylene of at least $1000 \times 10^{-6}$ sec$^{-1}$ when measured at a temperature of 100° C. and a mesitylene pressure of 2 torr.

Preferably, n is 20 to less than 60.

Preferably, X is aluminum and Y is silicon.

Preferably, the material has an alpha value in excess of 300.

In a further aspect, the invention resides a process for synthesizing the porous, crystalline ZSM-12 material of said one aspect of the invention comprising the steps of:

(a) preparing a mixture capable of forming said material, said mixture comprising sources of alkali or alkaline earth metal (M), an oxide of trivalent element (X), an oxide of tetravalent element (Y), hydroxyl (OH$^-$) ions, water and methyltriethylammonium cations (R), wherein said mixture has a composition, in terms of mole ratios, within the following ranges:

$YO_2/X_2O_3$=less than 100
$H_2O/YO_2$=10 to 100
$OH^-/YO_2$=0.1 to 0.6
$M/YO_2$=0.1 to 0.6
$R/YO_2$=0.1 to 0.6, (b) maintaining said mixture under sufficient conditions until crystals of said material are formed; and
(c) recovering said crystalline material from step (ii).

Preferably, said reaction mixture has a composition in terms of mole ratios within the following ranges:

$YO_2/X_2O_3$=40 to 80
$H_2O/YO_2$=15 to 40
$OH^-/YO_2$=0.15 to 0.4
$M/YO_2$=0.15 to 0.4
$R/YO_2$=0.15 to 0.4

Preferably, said conditions include a temperature of 140° C. to 170° C.

Preferably, M is sodium.

DETAILED DESCRIPTION OF THE EMBODIMENTS

Figure 1:
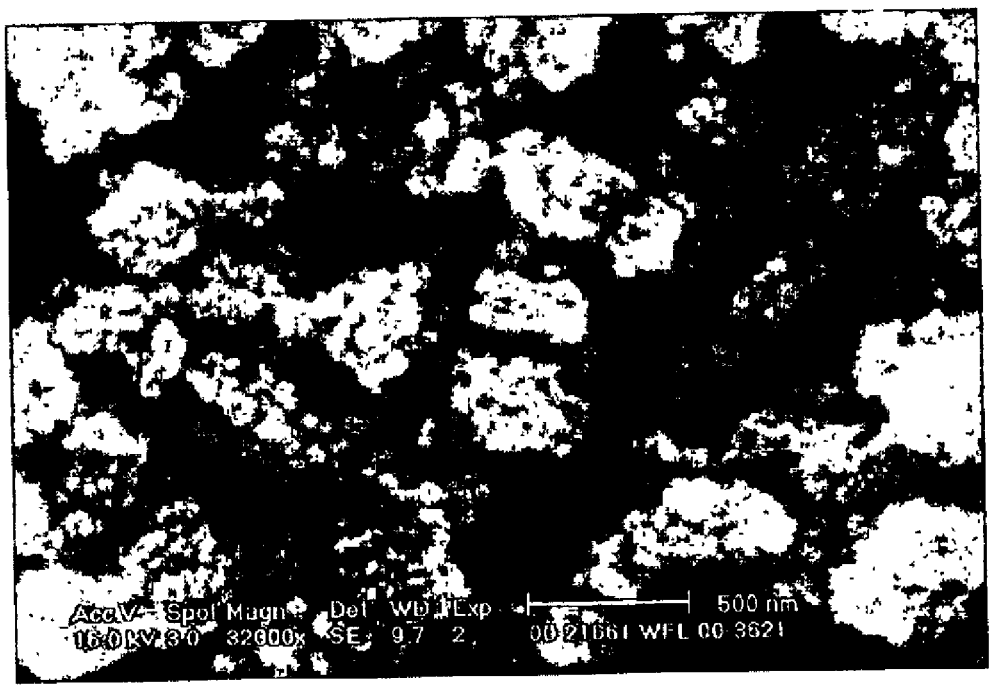
FIGS. 1 to 3 are scanning electron micrographs (SEM) of the as-synthesized products of Examples 1 to 3, respectively.

The ZSM-12 according to the invention has an X-ray diffraction pattern characterized by the X-ray diffraction lines in Table 1 below:

TABLE 1

| D-spacing (Å) | Relative Intensity [100 × I/Io] |
| --- | --- |
| 11.9 ± 0.2 | m |
| 10.1 ± 0.2 | m |
| 4.76 ± 0.1 | w |
| 4.29 ± 0.08 | vs |
| 3.98 ± 0.08 | m |
| 3.87 ± 0.07 | vs |
| 3.49 ± 0.07 | w |
| 3.38 ± 0.07 | m |
| 3.20 ± 0.06 | w |
| 3.05 ± 0.05 | w |
| 2.54 ± 0.03 | w |

These X-ray diffraction data were collected with a Scintag diffractometer using copper K-alpha radiation. The diffraction data were recorded by step-scanning at 0.02 degrees of two-theta, where theta is the Bragg angle, and a counting time of 1 second for each step. The interplanar spacings, d's, were calculated in Angstrom units (A), and the relative intensities of the lines, I/Io, where Io is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (75–100), s=strong (50–74), m=medium (25–49) and w=weak (0–24). It should be understood that diffraction data listed for this sample as single lines may consist of multiple overlapping lines which under certain conditions, such as differences in crystallite sizes or very high experimental resolution or crystallographic change, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history.

The crystalline material ZSM-12 of the present invention has a composition involving the molar relationship:

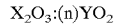

wherein X is a trivalent element, such as aluminum, boron, iron, indium and/or gallium, preferably aluminum; Y is a tetravalent element, such as silicon, tin and/or germanium, preferably silicon; and n is less than 60 and preferably from 20 to less than 60. In its as-synthesized form, the crystalline material of the invention has a formula, on an anhydrous basis and in terms of moles of oxides per n moles of $YO_2$, as follows:

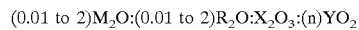

wherein M is an alkaline or alkaline earth metal, and is preferably sodium, and R is the methyltriethylammonium cation. The M and R components are associated with the material as a result of their presence during crystallization, and are easily removed by post-crystallization methods hereinafter more particularly described.

The ZSM-12 of the present invention has an average crystal size of the material is less than 0.1 micron, and preferably about 0.05 micron, and has a Diffusion Parameter, $D/r^2$, for mesitylene of at least $1000 \times 10^{-6}$ sec$^{-1}$, and preferably at least $2000 \times 10^{-6}$ sec$^{-1}$, when measured at a temperature of 100° C. and a mesitylene pressure of 2 torr.

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The ZSM-12 of the present invention preferably has an Alpha value of at least 150, and more preferably at least 300. The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The ZSM-12 of the present invention can be produced from a synthesis mixture containing sources of alkali or alkaline earth metal (M) cations, normally sodium, an oxide of a trivalent element (X), normally alumina, an oxide of a tetravalent element (Y), normally silica, methyltriethylammonium ions (R), normally present as the iodide salt, hydroxyl ions and water. The synthesis mixture has a composition, expressed in terms of mole ratios of oxides, as follows:

| Component | Useful | Preferred |
| --- | --- | --- |
| $YO_2/X_2O_3$ | 20–100 | 40–80 |
| $H_2O/YO_2$ | 10–100 | 15–40 |
| $OH^-/YO_2$ | 0.1–0.6 | 0.15–0.4 |
| $R/YO_2$ | 0.1–0.6 | 0.15–0.4 |
| $M/YO_2$ | 0.1–0.6 | 0.15–0.4 |

The synthesis method of the invention functions with or without added nucleating seeds. In a preferred embodiment, the reaction mixture contains 0.05–5 wt % nucleating seeds of ZSM-12.

Crystallization is carried out under either stirred or static conditions, preferably stirred conditions, at a relatively low temperature of 170° C. or less and preferably 140 to 160° C. Preferably, crystallization is conducted for 48 to 500 hours, whereafter the resultant ZSM-12 crystals are separated from the mother liquor and recovered.

In its as-synthesized form, the ZSM-12 of the invention contains the organic material(s) used as the directing agent and, prior to use as a catalyst or adsorbent, the as-synthesized material is normally treated to remove part or all of the organic constituent. This is conveniently effected by heating the as-synthesized material at a temperature of from about 250° C. to about 550° C. for from 1 hour to about 48 hours.

To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB and VIII of the Periodic Table of the Elements.

The crystalline material of this invention, when employed either as an adsorbent or as a catalyst in an organic compound conversion process should be dehydrated, at least partially. This can be done by heating to a temperature in the range of 200° C. to about 370° C. in an atmosphere such as air or nitrogen, and at atmospheric, subatmospheric or superatmospheric pressures for between 30 minutes and 48 hours. Dehydration can also be performed at room temperature merely by placing the ZSM-12 in a vacuum, but a longer time is required to obtain a sufficient amount of dehydration.

Synthetic ZSM-12 crystals prepared in accordance herewith can be used either in the as-synthesized form, the hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to the ZSM-12 such as, for example, by, in the case of platinum, treating the material with a platinum metal-containing ion. Suitable platinum compounds for this purpose include chloroplatinic acid, platinous chloride and various compounds containing the platinum amine complex. Combinations of metals and methods for their introduction can also be used.

When used as a catalyst, it may be desirable to incorporate the ZSM-12 of the invention with another material resistant to the temperatures and other conditions employed in certain organic conversion processes. Such matrix materials include active and inactive materials and synthetic or naturally occurring zeolites as well as inorganic materials such as clays, silica and/or metal oxides, e.g. alumina, titania and/or zirconia. The latter may be either naturally occurring or in the form of gelatinous precipitates, sols or gels including mixtures of silica and metal oxides. Use of a material in conjunction with the ZSM-12, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline catalytic materials have been incorporated into naturally occurring clays, e.g. bentonite and kaolin. These materials, i.e. clays, oxides, etc., function, in part, as binders for the catalyst. It is desirable to provide a catalyst having good crush strength because in a petroleum refinery the catalyst is often subjected to rough handling, which tends to break the catalyst down into powder-like materials which cause problems in processing.

Naturally occurring clays which can be composited with the hereby synthesized crystalline material include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the present crystals can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline material and matrix vary widely with the crystalline material content ranging from about 1 to about 90 percent by weight, and more usually in the range of about 2 to about 50 percent by weight of the composite.

Aluminosilicate ZSM-12 according to the invention is useful as a catalyst in organic compound, and in particular hydrocarbon, conversion reactions where high activity is important. In particular, when combined with a hydrogenation component, such as platinum, palladium or rhenium, the ZSM-12 is useful in the catalytic conversion of $C_9+$ alkylaromatic hydrocarbons, either alone or in the presence of toluene and/or benzene, to produce xylenes. Such conversion is typically effected at a temperature of from about 650 to about 950° F. (340 to 510° C.), and preferably from about 750 to about 850° F. (400 to 450° C.), a pressure of from about 100 to about 600 psig (790 to 4240 kPa), and preferably from about 200 to about 500 psig (1480 to 3550 kPa), a weight hourly space velocity (WHSV) of between about 0.1 and about 200 $hr^{-1}$, and preferably between about 0.5 and about 20 $hr^{-1}$, and a hydrogen, $H_2$, to hydrocarbon, HC, molar ratio of between about 1 and about 5, and preferably from about 1 to about 3.

Where the ZSM-12 of the invention is used in the catalytic conversion of $C_9+$ alkylaromatic hydrocarbons, the ZSM-12 may be used in combination with a second molecular sieve having a constraint index of 3 to 12, such as ZSM-5, ZSM-11, ZSM-22, ZSM-23, ZSM-35, ZSM-48, ZSM-57 and ZSM-58. The ZSM-12 and second molecular sieve may be arranged in separate catalyst beds, with the feed cascading from the catalyst bed containing the ZSM-12 to the bed containing the second molecular sieve. Alternatively, the ZSM-12 and second molecular sieve can be combined in a single catalyst bed.

In order to more fully illustrate the nature of the invention and the manner of practicing same, the following examples are presented.

EXAMPLE 1 (COMPARATIVE)

A mixture was prepared from 306 g of water, 83 g of 50% tetraethylammonium bromide (TEABr), 64.3 g of Ultrasil PM, 1.55 g of aluminum hydroxide and 15.8 g of 50% sodium hydroxide solution. The mixture had the following molar composition:

$SiO_2/Al_2O_3=100$
$H_2O/SiO_2=20$
$OH^-/SiO_2=0.2$
$Na^+/SiO_2=0.2$
$TEABr/SiO_2=0.2$

The mixture was reacted at 285° F. (140° C.) in a 600 ml autoclave with stirring at 150 RPM for 168 hours. The product was filtered, washed with deionized (DI) water and dried at 250° F. (120° C.). The XRD pattern of the as-synthesized material showed the typical pure phase of ZSM-12 topology. The SEM of the as-synthesized material is shown in FIG. 1 and shows that the material was composed of agglomerates of small crystals (with an average crystal size of about 0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 116, an Alpha value of 120, and a $D/r^2$ parameter for 1,3,5-trimethyl benzene (mesitylene) at 100° C. of $7,900 \times 10^{-6}$.

EXAMPLE 2 (COMPARATIVE)

The same reactants and procedure as Example 1 were used except that methyltriethylammonium (MTEA) bromide was used as the directing agent.

Figure 2:
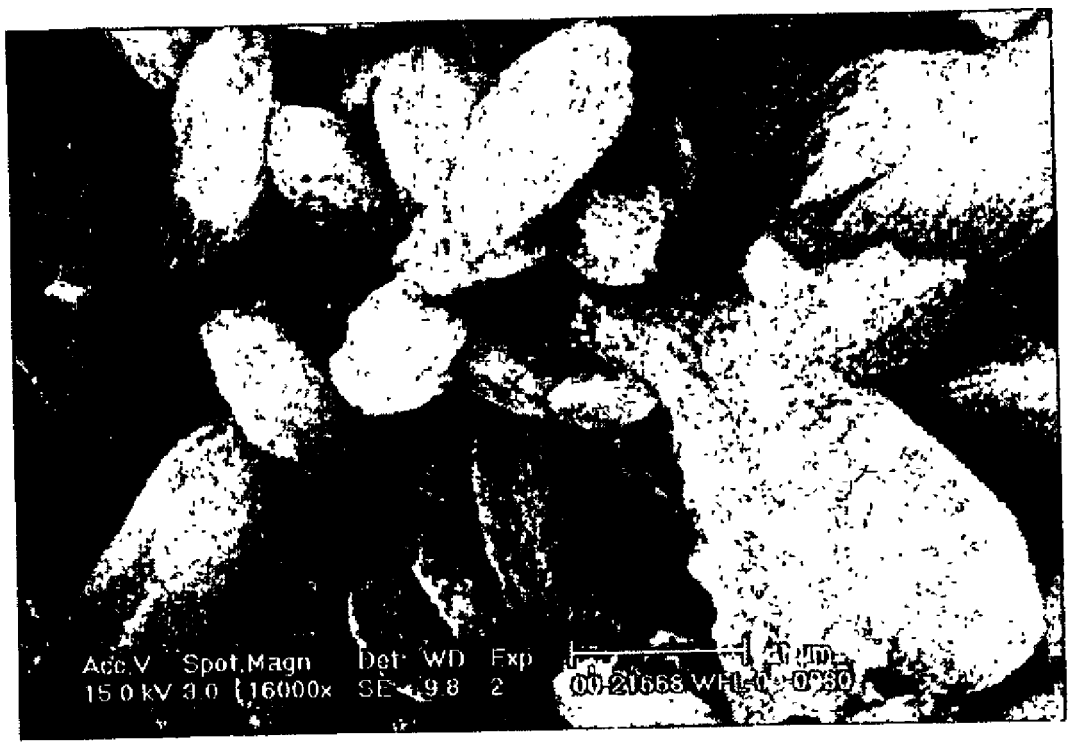

The SEM of the as-synthesized material is shown in FIG. 2 and shows that the material was composed of agglomerates of rice-shaped crystals (with an average crystal size of 1–5 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 116, an Alpha value of 92, and a $D/r^2$ parameter for 1,3,5-trimethyl benzene (mesitylene) at 100° C. of $19 \times 10^{-6}$.

EXAMPLE 3 (COMPARATIVE)

A mixture was prepared from 348 g of water, 30 g of methyltriethylammonium chloride (MTEACl), 64.3 g of Ultrasil PM, 2.33 g of Aluminum hydroxide, and 17.4 g of 50% sodium hydroxide solution. The mixture had the following molar composition:

$SiO_2/Al_2O_3=67$
$H_2O/SiO_2=20$
$OH^-/SiO_2=0.22$
$Na^+/SiO_2=0.22$
$MTEACl/SiO_2=0.2$

Figure 3:
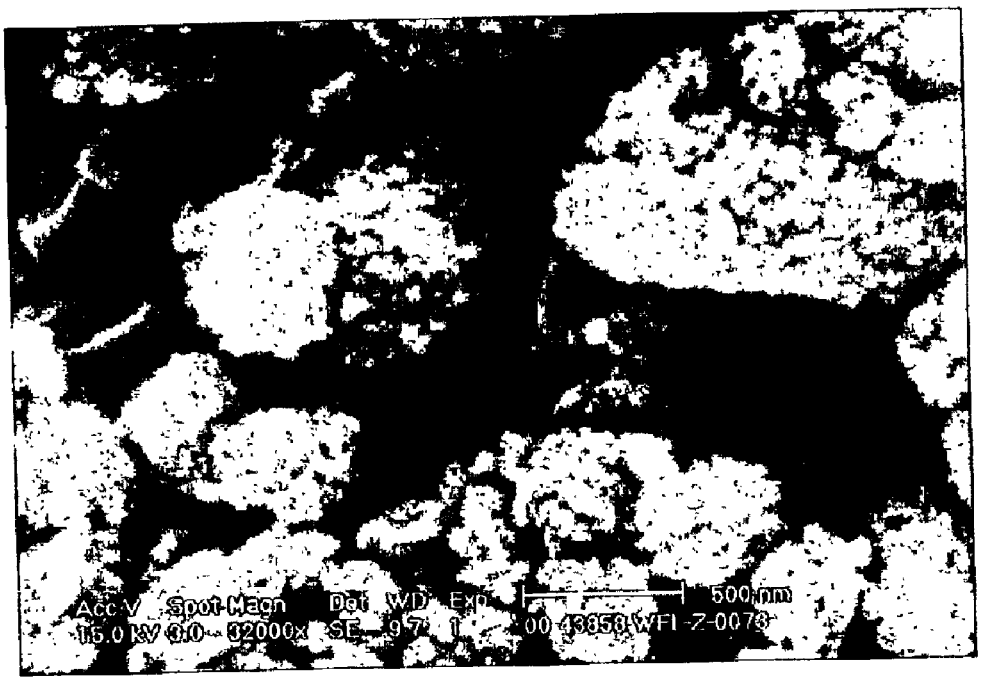

The mixture was reacted at 285° F. (140° C.) in a 600 ml autoclave with stirring at 150 RPM for 168 hours. The product was filtered, washed with deionized (DI) water and dried at 250° F. (120° C.). The XRD pattern of the as-synthesized material showed the typical pure phase of ZSM-12 topology. The SEM of the as-synthesized material is shown in FIG. 3 and shows that the material was composed of agglomerates of small crystals (with an average crystal size of about 0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 68.6, an Alpha value of 190, and a $D/r^2$ parameter for 1,3,5-trimethyl benzene (mesitylene) at 100° C. of $600 \times 10^{-6}$.

EXAMPLE 4

A mixture was prepared from 1158 g of water, 85 g of methyltriethylammonium chloride (MTEACl), 178 g of Ultrasil PM, 17 g of sodium aluminate solution (45%), and 35 g of 50% sodium hydroxide solution. The mixture had the following molar composition:

$SiO_2/Al_2O_3=60$
$H_2O/SiO_2=24.5$
$OH^-/SiO_2=0.2$
$Na^+/SiO_2=0.2$
$MTEACl/SiO_2=0.21$

The mixture was reacted at 320° F. (160° C.) in a 2 liter autoclave with stirring at 150 RPM for 168 hours. The product was filtered, washed with deionized (DI) water and dried at 250° F. (120° C.). The XRD pattern of the as-synthesized material showed the typical pure phase of ZSM-12 topology. The SEM of the as-synthesized material was similar to that shown in FIG. 3 and showed that the material was composed of agglomerates of small crystals (with an average crystal size of about 0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 58.1, an Alpha value of 340, and a $D/r^2$ parameter for 1,3,5-trimethyl benzene (mesitylene) at 100° C. of $1150 \times 10^{-6}$.

EXAMPLE 5

A mixture was prepared from 1204 g of water, 105 g of methyltriethylammonium Bromide (MTEABr), 283 g of sodium silicate solution, 16.8 g of aluminum nitrate and 16.45 of sulfuric acid (98% solution). The mixture had the following molar composition:

$SiO_2/Al_2O_3=60$
$H_2O/SiO_2=57$
$OH^-/SiO_2=0.3$
$Na^+/SiO_2=0.6$
$MTEABr/SiO_2=0.4$

The mixture was reacted at 320° F. (160° C.) in a 2 liter autoclave with stirring at 150 RPM for 120 hours. The product was filtered, washed with deionized (DI) water and dried at 250° F. (120° C.). The XRD pattern of the as-synthesized material showed the typical pure phase of ZSM-12 topology. The SEM of the as-synthesized material was similar to that shown in FIG. 3 and shows that the material was composed of agglomerates of small crystals (with an average crystal size of about 0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 51.8, an Alpha value of 330, and a $D/r^2$ parameter for 1,3,5-trimethyl benzene (mesitylene) at 100° C. of $1400 \times 10^{-6}$.

EXAMPLE 6

A mixture was prepared from 1185 g of water, 98 g of methyltriethylammonium chloride (MTEACl), 204.5 g of Ultrasil PM, 24 g of sodium aluminate solution (45%), and 43.2 g of 50% sodium hydroxide solution. The mixture had the following molar composition:

$SiO_2/Al_2O_3=50$
$H_2O/SiO_2=22$
$OH^-/SiO_2=0.22$
$Na^+/SiO_2=0.22$
$MTEACl/SiO_2=0.2$

The mixture was reacted at 285° F. (140° C.) in a 2 liter autoclave with stirring at 150 RPM for 336 hours. The product was filtered, washed with deionized (DI) water and dried at 250° F. (120° C.). The XRD pattern of the as-synthesized material showed the typical pure phase of ZSM-12 topology. The SEM of the as-synthesized material was similar to that shown in FIG. 3 and shows that the material was composed of agglomerates of small crystals (with an average crystal size of about 0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 46.3, an Alpha value of 472, and a $D/r^2$ parameter for 1,3,5-trimethyl benzene (mesitylene) at 100° C. of $3600 \times 10^{-6}$.

EXAMPLE 7

Figure 4:
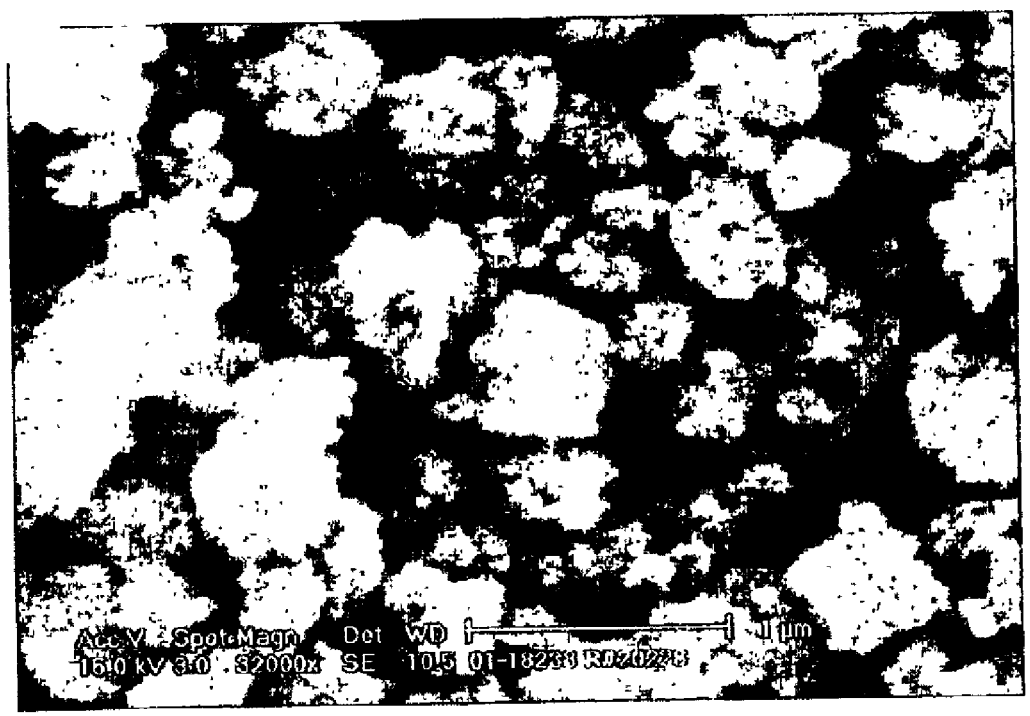
FIG. 4 is a scanning electron micrograph (SEM) of the as-synthesized product of Example 7.

A reaction mixture having the same composition as in Example 3 was combined with 0.5 wt % of seeds of ZSM-12 as produced in Example 3 and was reacted at 320° F. (160° C.) in a 5 gallon autoclave with stirring at 150 RPM for 120 hours. The product was filtered, washed with DI water and dried at 120° C. The XRD pattern of the as-synthesized material showed the typical pure phase of ZSM-12 topology. The SEM of the as-synthesized material is shown in FIG. 4 and shows that the material was composed of agglomerates of small crystals (with an average crystal size of about 0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 48.2, an Alpha value of 560, and a $D/r^2$ parameter for 1,3,5-trimethyl benzene (mesitylene) at 100° C. of $8,450 \times 10^{-6}$.

Figure 5:
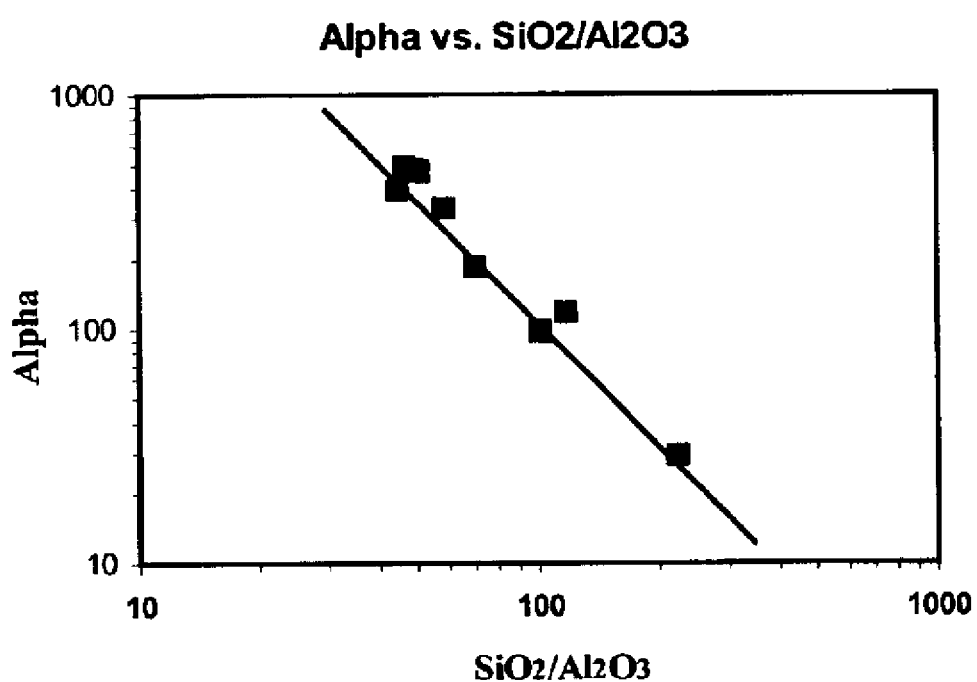
FIG. 5 is a graph plotting the $SiO_2/Al_2O_3$ against the alpha activity of the hydrogen forms of the ZSM-12 products of Examples 1 to 7.

The relative activity and the $SiO_2/Al_2O_3$ composition of the ZSM-12 crystals of Examples 1 to 7 are plotted in FIG. 5. It will be seen from FIG. 5 that ZSM 12 crystals with $SiO_2/Al_2O_3 < 60$ and the desired morphology in the form of agglomerates of small crystals, can be produced by using MTEA hydroxide or their salts at 260–320° F. (140–160° C.) under stirred conditions.

EXAMPLE 8

A ZSM-12/alumina catalyst was prepared from 65 parts of H-form ZSM-12 crystal produced in Example 5 mixed with 35 parts of LaRoche Versal 300 alumina on a dry basis. The mixture was mulled and formed into ¹⁄₁₆" cylindrical extrudates. The prepared extrudates were dried at 250° F. (120° C.) and calcined at 1000° F. (540° C.) for 6 hours. The finished extrudate had an alpha of 316.

The finished extrudate was then impregnated with an ammonium perrhenate (APR) solution via incipient wetness impregnation to give 0.5 wt % Re on the extrudate. The extrudate was dried at 250° F. (120° C.) for 2 hours and then calcined in air for 1 hour at 975° F. (524° C.). The impregnated and calcined extrudate was steamed in 100% steam at 900° F. (482° C.) for 5.5 hours. The final catalyst contained 0.44 wt % Re and had an alpha value of 60.

EXAMPLE 9

The catalyst prepared in Example 8 was tested in the catalytic conversion of a $C_9$+ aromatics feed containing about 60 wt % toluene and having the precise composition given in Table 2 below. The catalytic evaluations were performed in a microunit having a ⅜" (9.5 mm) external diameter reactor tube, into which was loaded catalyst, mixed with sand as a packing material. After loading in the reactor, the catalyst was dried at 200° C. for 2 hours and reduced with hydrogen for 1 hour at 427° C. and a hydrogen pressure of 340 psig (2445 kPa). The reactor was then heated under nitrogen to the reaction temperature of 427° C. and the reaction was conducted at a pressure of 340 psig (2445 kPa), a hydrogen to hydrocarbon molar ratio of 1.2 and a WHSV of 3–6. The results are summarized in Table 2 below.

TABLE 2

| | | | | | | | | |
|---|---|---|---|---|---|---|---|---|
| WHSV | | 6.00 | 3.00 | 3.00 | 3.00 | 3.00 | 3.00 | 3.00 |
| Days on Stream | | 1.13 | 1.90 | 2.83 | 3.83 | 4.83 | 5.42 | 6.42 |
| Yields, wt % | FEED | | | | PRODUCT | | | |
| Methane | | 1.27 | 1.06 | 1.27 | 0.33 | 0.08 | 0.08 | 0.08 |
| C2 | | 2.09 | 2.22 | 2.09 | 2.16 | 2.09 | 2.09 | 2.09 |
| Propylene | | 1.16 | 1.19 | 1.16 | 1.46 | 1.51 | 1.51 | 1.51 |
| C4 | | 0.70 | 0.55 | 0.68 | 0.68 | 0.74 | 0.64 | 0.70 |
| C5 | | 0.11 | 0.08 | 0.11 | 0.07 | 0.08 | 0.08 | 0.08 |
| C6 non-A | | 0.36 | 0.36 | 0.27 | 0.27 | 0.27 | 0.27 | 0.30 |
| C7 non-A | | 0.02 | 0.01 | 0.02 | 0.01 | 0.01 | 0.01 | 0.01 |
| Benzene | | 9.43 | 9.58 | 11.19 | 11.35 | 11.60 | 11.47 | 11.76 |
| Toluene | 62.95 | 39.87 | 39.97 | 36.60 | 36.37 | 36.72 | 36.52 | 37.84 |
| Ethylbenzene | 0.05 | 1.59 | 1.65 | 1.11 | 1.06 | 1.12 | 1.09 | 1.31 |
| Xylenes | 3.26 | 26.98 | 26.80 | 31.09 | 31.54 | 31.30 | 31.53 | 29.46 |
| Cumene | 0.34 | 0.01 | 0.01 | 0.01 | 0.01 | 0.00 | 0.01 | 0.01 |
| n-propylbenzene | 1.05 | 0.01 | 0.01 | 0.01 | 0.01 | 0.01 | 0.01 | 0.01 |
| Ethyltoluenes | 12.72 | 3.53 | 3.68 | 1.79 | 1.77 | 1.77 | 1.80 | 2.28 |
| Trimethylbenzenes | 18.58 | 10.16 | 10.05 | 9.64 | 9.91 | 9.70 | 9.85 | 9.54 |
| Diethylbenzenes | 0.37 | 0.06 | 0.07 | 0.03 | 0.03 | 0.03 | 0.03 | 0.04 |
| Dimethylethylbenzenes | 0.44 | 0.74 | 0.77 | 0.54 | 0.55 | 0.55 | 0.56 | 0.63 |
| Tetramethylbenzenes | 0.00 | 0.50 | 0.49 | 0.64 | 0.67 | 0.65 | 0.66 | 0.58 |
| Indan | 0.21 | 0.33 | 0.34 | 0.25 | 0.26 | 0.25 | 0.26 | 0.28 |
| Methylindans | | 0.08 | 0.08 | 0.10 | 0.11 | 0.10 | 0.10 | 0.09 |
| Naphthalene | | 0.08 | 0.08 | 0.08 | 0.08 | 0.08 | 0.08 | 0.08 |
| Methylnaphthalenes | | 0.22 | 0.22 | 0.35 | 0.37 | 0.35 | 0.36 | 0.34 |
| Other | 0.05 | 0.70 | 0.72 | 0.96 | 0.93 | 0.99 | 1.02 | 1.01 |
| Toluene Conversion (wt %) | | 36.66 | 36.50 | 41.87 | 42.22 | 41.66 | 41.98 | 39.90 |
| $A_9$ + Conversion (wt %) | | 51.59 | 51.26 | 57.83 | 56.80 | 57.40 | 56.77 | 56.30 |

TABLE 2-continued

| | | | | | | | | |
|---|---|---|---|---|---|---|---|---|
| Toluene + A9 + Conversion (wt %) | | 41.88 | 41.61 | 47.47 | 47.20 | 47.02 | 47.03 | 45.48 |
| BTX (wt %) | 66.21 | 76.28 | 76.35 | 78.88 | 79.27 | 79.63 | 79.52 | 79.05 |
| Benzene Purity (% C6) | | 96.36 | 96.39 | 97.61 | 97.67 | 97.73 | 97.67 | 97.52 |
| Ring Loss (mol %) | | 4.02 | 3.76 | 3.73 | 3.09 | 2.80 | 2.82 | 2.64 |
| Hydrogen Consumption (%) | | 13.42 | 11.23 | 10.77 | 4.39 | 1.98 | 1.73 | 1.43 |

EXAMPLE 10

The process of Example 10 was repeated but with the catalyst being steamed at 900° F. (482° C.) for 5.5 hours before being contacted with the same feed as used in Example 10. Process conditions were as in Example 10 and the results are summarized in Table 3 below.

TABLE 3

| | | | | | |
|---|---|---|---|---|---|
| WHSV | 6 | 6 | 6 | 3 | 3 |
| Days on Stream | 1.13 | 1.90 | 2.83 | 3.83 | 4.83 |
| Yields, wt % | | | | | |
| Methane | 1.27 | 1.06 | 1.27 | 0.33 | 0.08 |
| C2 | 2.09 | 2.21 | 2.09 | 2.15 | 2.09 |
| Propylene | 1.16 | 1.19 | 1.16 | 1.45 | 1.51 |
| C4 | 0.81 | 0.78 | 0.75 | 0.92 | 0.78 |
| C5 | 0.11 | 0.08 | 0.11 | 0.07 | 0.08 |
| C6 non-A | 0.37 | 0.37 | 0.37 | 0.34 | 0.32 |
| C7 non-A | 0.02 | 0.01 | 0.02 | 0.01 | 0.01 |
| Benzene | 10.39 | 10.27 | 10.29 | 11.23 | 11.60 |
| Toluene | 36.92 | 36.65 | 37.33 | 40.86 | 36.67 |
| Ethylbenzene | 1.73 | 1.74 | 1.79 | 1.40 | 1.37 |
| Xylenes | 29.12 | 29.28 | 28.65 | 26.23 | 30.25 |
| n-propylbenzene | 0.01 | 0.01 | 0.01 | 0.00 | 0.01 |
| Ethyltoluenes | 3.38 | 3.43 | 3.51 | 1.04 | 2.43 |
| Trimethylbenzenes | 9.96 | 10.13 | 9.98 | 10.84 | 9.98 |
| Propyltoluenes | 0.00 | 0.00 | 0.00 | 0.04 | 0.00 |
| Diethylbenzenes | 0.07 | 0.07 | 0.07 | 0.01 | 0.04 |
| Dimethylethylbenzenes | 0.77 | 0.78 | 0.77 | 0.70 | 0.65 |
| Tetramethylbenzenes | 0.51 | 0.52 | 0.49 | 0.65 | 0.58 |
| Indan | 0.34 | 0.35 | 0.35 | 0.33 | 0.31 |
| Methylindans | 0.08 | 0.08 | 0.08 | 0.10 | 0.09 |
| Naphthalene | 0.09 | 0.09 | 0.09 | 0.10 | 0.09 |
| Methylnaphthalenes | 0.18 | 0.19 | 0.18 | 0.27 | 0.25 |
| Other | 0.63 | 0.69 | 0.64 | 0.93 | 0.82 |
| Toluene Conversion (wt %) | 41.35 | 41.77 | 40.69 | 35.09 | 41.74 |
| A9 + Conversion (wt %) | 52.77 | 51.63 | 52.35 | 55.91 | 55.06 |
| Toluene + A9 + Conversion (wt %) | 45.31 | 45.11 | 44.75 | 42.14 | 46.23 |
| BTX (wt %) | 76.43 | 76.20 | 76.27 | 78.32 | 78.51 |
| Benzene Purity (% C6) | 96.59 | 96.55 | 96.50 | 97.05 | 97.30 |
| Ring Loss (mol %) | 4.15 | 4.20 | 4.10 | 2.87 | 2.89 |
| Hydrogen Consumption (%) | 14.40 | 12.93 | 14.08 | 4.17 | 3.46 |

We claim:

1. A porous, crystalline material having the framework structure of ZSM-12 and a composition involving the molar relationship:

$$X_2O_3:(n)YO_2$$

wherein X is a trivalent element, Y is a tetravalent element and n is less than 60, wherein the average crystal size of the material is less than 0.1 micron and wherein the material has a Diffusion Parameter for mesitylene of at least $1000 \times 10^{-6}$ sec$^{-1}$ when measured at a temperature of 100° C. and a mesitylene pressure of 2 torr.

2. The porous, crystalline material of claim 1, wherein n is 20 to less than 60.

3. The porous, crystalline material of claim 1, wherein X is aluminum and Y is silicon.

4. The porous, crystalline material of claim 1, wherein said material has an alpha value in excess of 150.

5. The porous, crystalline material of claim 1, wherein said material has an alpha value in excess of 300.

6. A process for synthesizing the porous, crystalline material of claim 1, comprising the steps of:

(a) preparing a mixture capable of forming said material, said mixture comprising sources of alkali or alkaline earth metal (M), an oxide of trivalent element (X), an oxide of tetravalent element (Y), hydroxyl (OH⁻) ions, water and methyltriethylammonium cations (R), wherein said mixture has a composition, in terms of mole ratios, within the following ranges:

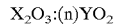=less than 100

$H_2O/YO_2$=10 to 100

$OH^-/YO_2$=0.1 to 0.6

$M/YO_2$=0.1 to 0.6

$R/YO_2$=0.1 to 0.6, (b) maintaining said mixture under sufficient conditions until crystals of said material are formed; and (c) recovering said crystalline material from step (ii).

7. The process of claim 6, wherein said reaction mixture has a composition in terms of mole ratios within the following ranges:

$YO_2/X_2O^3$=40 to 80

$H_2O/YO_2$=15 to 40

$OH^-/YO_2$=0.15 to 0.4

$M/YO_2$=0.15 to 0.4

$R/YO_2$=0.15 to 0.4.

8. The process of claim 6, wherein said conditions include a temperature of 170° C. or less.

9. The process of claim 6, wherein said conditions include a temperature of 140° C. to 160° C.

10. The process of claim 6, wherein M is sodium.

11. A process for converting C9+ alkylaromatic hydrocarbons to a product including xylenes, comprising the step of contacting a feed containing C9+ alkylaromatic hydrocarbons together with toluene and/or benzene under conversion conditions with the porous crystalline material of claim 1.

12. The process of claim 11, wherein n is 20 to less than 60.

13. The process of claim 11, wherein X is aluminum and Y is silicon.

14. The process of claim 11, wherein said porous, crystalline material has an alpha value in excess of 150.

15. The process of claim 11, wherein said porous, crystalline material has an alpha value in excess of 300.

16. The process of claim 11, wherein said conversion conditions include a temperature of from about 650 to about 950° F. (340 to 510° C.), a pressure of from about 100 to about 600 psig (790 to 4240 kPa), a weight hourly space velocity of between about 0.1 and about 200 hr$^{-1}$, and a hydrogen to hydrocarbon molar ratio of between about 1 and about 5.

17. The process of claim 11, wherein said conversion conditions include a temperature of from about 750 to about 850° F. (400 to 450° C.), a pressure of from about 200 to about 500 psig (1480 to 3550 kPa), a weight hourly space velocity between about 0.5 and about 20 hr$^{-1}$, and a hydrogen to hydrocarbon molar ratio of between about 1 to about 3.

18. The process of claim 11, wherein said feed is also contacted with a second molecular sieve having a constraint index of 3 to 12.

19. The process of claim 18, wherein said second molecular sieve is selected from ZSM-5, ZSM-11, ZSM-22, ZSM-23, ZSM-35, ZSM-48, ZSM-57 and ZSM-58.

* * * * *